United States Patent [19]

Elmovist

[11] Patent Number: 4,463,760

[45] Date of Patent: Aug. 7, 1984

[54] IMPLANTABLE HEART PACEMAKER

[75] Inventor: Hakan Elmovist, Bromma, Sweden

[73] Assignee: Siemens Aktiengesellschaft, Berlin & Munich, Fed. Rep. of Germany

[21] Appl. No.: 404,713

[22] Filed: Aug. 3, 1982

[30] Foreign Application Priority Data

Aug. 4, 1981 [DE] Fed. Rep. of Germany ....... 3130872

[51] Int. Cl.³ .............................................. A61N 1/36
[52] U.S. Cl. ............................................ 128/419 PG
[58] Field of Search ................................. 128/419 PG

[56] References Cited

U.S. PATENT DOCUMENTS

| | | | |
|---|---|---|---|
| 3,842,844 | 10/1974 | Alferness | 128/422 |
| 3,901,247 | 8/1975 | Walmsley | 128/419 PG |
| 4,114,628 | 9/1978 | Rizk | 128/419 PG |
| 4,423,733 | 1/1984 | Grassi et al. | 128/419 PG |

*Primary Examiner*—William E. Kamm
*Assistant Examiner*—Mitchell J. Shein
*Attorney, Agent, or Firm*—Hill, Van Santen, Steadman & Simpson

[57] ABSTRACT

As the battery of a heart pacemaker is discharged, its internal resistance rises, as a result of which the amplitude of the stimulation pulses decreases. In order to still be able to generate stimulation pulses with an amplitude which lies above the threshold of the heart even given a battery which has already been largely discharged, it is inventively provided that the discharge of the output capacitor can only be triggered given attainment of a specific minimum voltage ($V_{min}$) at said output capacitor. That can be advantageously executed with the assistance of a comparator which compares the voltage at the capacitor to a comparison voltage ($V_{min}$) and which inhibits the actuation of a switch via a NOR gate until matching has been achieved. The base frequency of the heart pacemaker and the pulse width can be fixed by two monostable flip-flops.

4 Claims, 2 Drawing Figures

IMPLANTABLE HEART PACEMAKER

BACKGROUND OF THE INVENTION

The invention relates to an implantable heart pacemaker comprising a battery whose internal resistance depends on the charge condition of the battery, as well as comprising a stimulus pulse generator connected to the battery having an output capacitor which is respectively slowly charged and is subsequently rapidly discharged for generating a stimulation pulse.

Such modern, implantable heart pacemakers employ batteries with a constant electromotive force whose internal resistance increases the more greatly the battery is discharged. That leads to the fact that the amplitude of the stimulation pulses decreases with an increasing discharge of the battery, since the output capacitor must be charged with a current which becomes smaller and smaller and, thus, can no longer reach its full voltage in the time available for charging. When the amplitude of the stimulation pulses falls below the threshold value characteristic for the patient, the stimulation pulses become ineffective.

Attempts have already been undertaken to extend the operating life of such a heart pacemaker in that the width of the stimulation pulses is increased as the battery discharges (German OS No. 2,301,055). Since, however, the threshold can only be influenced to a very slight degree by the width of the stimulation pulses, only an insignificant prolongation of the useful life can be achieved in this manner. Beyond that, the disadvantage of an increased power consumption per pulse derives given this method as, thus, does an accelerated discharge of the battery.

SUMMARY OF THE INVENTION

Given a heart pacemaker of the type initially cited, the object of the present invention is to see to it that, even given a progressive discharge of the battery, a certain minimum amplitude of the stimulation pulses is always made available for a reliable stimulation of the heart and that, simultaneously, an indication of the incipient critical condition of the battery is supplied.

This object is inventively achieved in that the discharge of selected pulses is only triggerable when a specific minimum voltage $V_{min}$ is reached at the output capacitor. As a result, the heart pacemaker emits pulses which at least exhibit the set, minimum amplitude. Since these lie above the threshold, the heart is certain to be stimulated. When it is a matter, for example, of a heart pacemaker which functions with a specific, adjustable base frequency, then this base frequency can be maintained until the charging time thereby determined no longer suffices given an increasing internal resistance of the battery in order to charge the output capacitor to the minimum voltage which has been set. With an increasing internal battery resistance, the frequency then automatically begins to drop in such manner that the amplitude of the output pulses constantly corresponds to the minimum value. Thereby, the minimum amplitude can be guaranteed for each pulse. However, this can also be foregone for individual pulses.

It is provided in an advantageous further development of the invention that the minimum voltage $V_{min}$ is adjustable. Particularly, given modern, programmable heart pacemakers, this voltage should also be programmable. The control of the pulse generator can ensue both analog as well as digital.

Since, given the inventive heart pacemaker, the frequency remains constant up to a certain limiting value of the internal battery resistance and then begins to continuously drop, the bend in the frequency curve represents a reliable mark for the charge condition of the battery.

An advantageously simple and reliable embodiment of an inventive heart pacemaker with a known short-circuiting switch, particularly with a transistor switch, derives in that the switch is actuatable by means of a monostable flip-flop whose switching time $t_m$ lies in the range of the desired discharge duration. The input of said monostable flip-flop is connected to the output of a NOR gate whose one input is connected to the output of a further monostable flip-flop with a switching time determining a base frequency of the heart pacemaker and whose other input is connected to the output of a comparator. The output of the first monostable flip-flop is in turn connected to the input of the further monostable flip-flop. The minimum voltage $V_{min}$ is supplied to one input of the comparator and the voltage of the output capacitor is supplied to the other input. The further monostable flip-flop thereby determines the base frequency and, thus, the charging time for the output capacitor as well. When the voltage at the output capacitor reaches the minimum voltage $V_{min}$ in this time or even exceeds it, then, at the end of the switching time of the further monostable flip-flop, the first monostable flip-flop is driven and the output capacitor is short-circuited for a brief duration. When in contrast thereto, the charging voltage at the output capacitor does not reach the minimum voltage in the prescribed switching time, then the first monostable flip-flop and, thus, the short-circuiting of the output capacitor is inhibited until the voltage has reached the minimum value. The amplitude of the stimulation pulses can therefore never drop below the minimum voltage $V_{min}$. In contrast to known heart pacemakers given which the pulse width of the stimulation pulses is increased given an increased internal battery resistance, the power consumption per time unit simultaneously decreases given a decreasing frequency. A further advantage of the inventive heart pacemaker consists in a certain protection against an uncontrolled increase of the heart pacemaker frequency due to an occurring error. The pulses can always only be emitted when the voltage at the capacitor exceeds the minimum voltage.

An exemplary embodiment of the invention is described and explained in greater detail below on the basis of two Figures on the accompanying drawing sheet, and other objects, features and advantages will be apparent from this detailed disclosure and from the appended claims.

DETAILED DESCRIPTION

Figure 1:
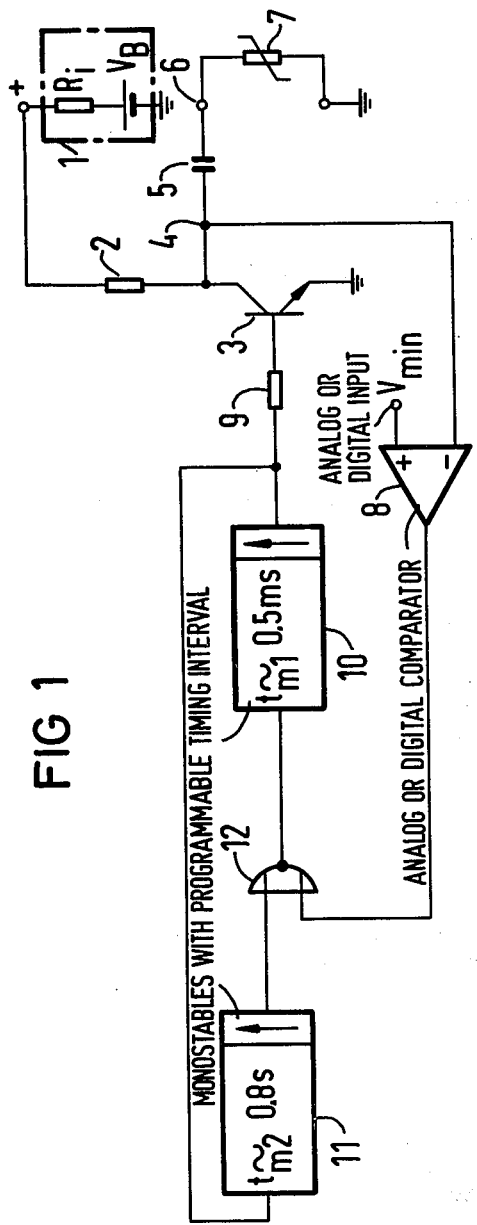
FIG. 1 in a block diagram, shows the most significant parts for illustrating the inventive heart pacemaker.

A battery 1 with an internal resistance $R_i$ dependent on its charge condition is illustrated with dot-dash lines in FIG. 1. The open circuit (no load) voltage of the battery is referenced with $V_B$. One pole of the battery lies at ground, i.e., it is connected to the body of the patient. The other pole is connected via a fixed resistor 2 to the collector of a transistor 3 and to a terminal 4 of the output capacitor 5. The other terminal 6 of the capacitor 5 is connected via an electrode to the heart of the patient, here illustrated as a variable resistor 7. The circuit is closed through the body of the patient. Further, the terminal 4 is connected to the inverting input of a comparator 8 to whose noninverting input a comparison voltage $V_{min}$ is applied. The emitter of the transistor 3 is connected to ground; the base is connected via a resistor 9 to the output of a monostable flip-flop 10 having a switching time $t_{ml}$ of approximately one-half millisecond (0.5 ms). The output of said monostable flip-flop 10 is simultaneously connected to the input of a further monostable flip-flop 11 with a switching time $t_{m2}$ of approximately eight-tenths of a second (0.8 s). The outputs of said further monostable flip-flop 11 and of the comparator 8 are connected to inputs of a NOR gate 12 whose output drives the first monostable flip-flop 10. The manner of functioning of said circuit is as follows:

The two monostable flip-flops are situated in their initial position, i.e., the outputs lie at a low potential. As a result, the transistor 3 is blocked and the capacitor 5 slowly charges via the resistor 2. As long as the voltage at the capacitor 5 has not yet reached the comparison voltage $V_{min}$, the output of the comparator 8 lies at high potential. As a result, different potentials lie at the inputs of the NOR gate 12 and the output value of said gate lies at zero. When the voltage at the capacitor 5 reaches the comparison voltage $V_{min}$, then the output voltage of the comparator 8 becomes low so that a logical zero is adjacent to both inputs of the NOR gate. The output of the NOR gate thus becomes logical one, as a result of which the monostable flip-flop is transferred into its active condition for the switching time $t_{m1}$. During this time, the output of said monostable flip-flop 10 exhibits a high potential, as a result of which the transistor 3 is switched to conductive mode. The capacitor 5 can quickly discharge via the transistor 3, whereby a stimulation pulse is supplied to the heart. Simultaneously, when the monostable flip-flop 10 switches, the further monostable flip-flop 11 is started, whereby its output assumes a logical one for the switching time $t_{m2}$. The NOR gate 12 is thus blocked again.

As long as the internal resistance $R_i$ is still so small that the voltage at the capacitor 5 reaches and even exceeds the comparison voltage $V_{min}$ in the switching time $t_{m2}$ of the monostable flip-flop 11, the frequency of the stimulation pulses is fixed by the switching time of said monostable flip-flop 11. When the internal resistance $R_i$ of the battery 1 has increased to such degree that the voltage at the capacitor 5 has not yet reached the comparison voltage $V_{min}$ in the switching time $t_{m2}$, then the NOR gate 12 blocks until the comparison voltage has been reached. It is only then that the monostable flip-flop 10 is started and the transistor 3 is switched to conductive mode. The frequency of the stimulation pulses therefore decreases from that point in time with an increasing internal resistance $R_i$ of the battery.

In order to change the base frequency of the heart pacemaker, the switching time $t_{m2}$ of the monostable flip-flop 11 can be variable. Likewise, the comparison voltage $V_{min}$ can be designed variable. These and other magnitudes can advantageously be programmable.

Figure 2:
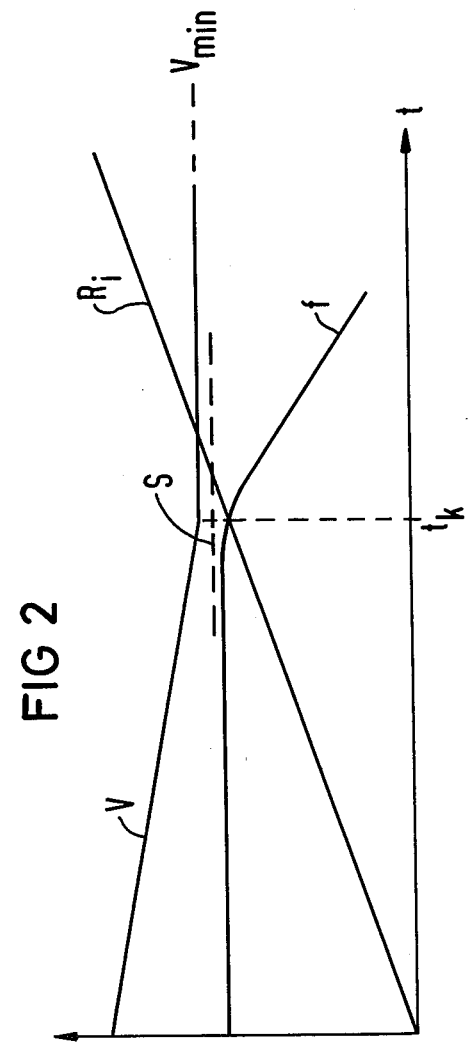
FIG. 2 is a graphical illustration showing the chronological progression of various characteristics such as, for example, the frequency.

Illustrated in an arbitrary scale in FIG. 2 is a diagram of the chronological progression of the frequency f of the heart pacemaker, of the amplitude v of the stimulation pulses, as well as of the internal resistance of the battery. As one can derive from said diagram, the internal resistance $R_i$ of the battery 1 increases linearly with the time. At the same time, the amplitude of the stimulation pulses descreases. As long as said amplitude, however, still lies above the minimum voltage $V_{min}$, the frequency of the heart pacemaker remains unaltered. At a specific point in time $t_k$, the amplitude would normally fall below the minimum voltage $V_{min}$ so that the reliable stimulation of the heart by the stimulation pulse would no longer be guaranteed. As a result of the inventive circuit arrangement, the frequency of the stimulation pulses begins to decrease from this point in time in such manner that the voltage at the capacitor 5 and, thus, the amplitude of the stimulation pulses, constantly corresponds to the minimum voltage $V_{min}$. Further, the threshold S of the heart is indicated with broken lines in this diagram in order to show that the amplitude of the stimulation pulses is always greater than the threshold.

It will be apparent that many modifications and variations may be made without departing from the scope of the teachings and concepts of the present invention.

I claim as my invention:

1. An implantable heart pacemaker comprising a battery whose internal resistance depends on the charge condition of the battery, as well as comprising a stimulus pulse generator connected to the battery having an output capacitor which is respectively slowly charged and subsequently rapidly discharged in order to generate a stimulation pulse, control means comprising a control circuit connected with said stimulus pulse generator for triggering said stimulus pulse generator, said control means further comprising comparator means having an input coupled with said output capacitor for comparing a voltage at said output capacitor with a specific minimum voltage ($V_{min}$) and having an output coupled with said control circuit such that the discharge of the output capacitor to produce selected stimulation pulses is only triggered upon the attainment of the specific minimum voltage ($V_{min}$) at the output capacitor.

2. A heart pacemaker according to claim 1, characterized in that the minimum voltage ($V_{min}$) is adjustable.

3. A heart pacemaker according to claim 1, wherein said comparator means is responsive to the analog voltage at the output capacitor (5), said comparator means including analog to digital converter means, and digital means coupled with said comparator means for supplying a digital signal corresponding to the minimum voltage ($V_{min}$).

4. A heart pacemaker according to claim 1, said generator comprising transistor switch means for discharging the output capacitor, additionally said control means comprising a first monostable circuit (10) controlling said switch (3), said first monostable circuit (10) having a switching time ($t_{mi}$) in the range of the desired discharge duration, a NOR gate (12) controlling said first monostable circuit (10), a further monostable circuit (11) having an output connected with the NOR gate (12), said further monostable circuit (11) having a switching time ($t_{m2}$) fixing a limiting frequency of the heart pacemaker, and comparator means having an output connected with the NOR gate (12), the output of the first monostable flip-flop (10) being connected to the input of the further monostable flip-flop (11), and means for supplying a minimum voltage signal ($V_{min}$) at one input of the comparator means (8) and the voltage of the output capacitor (5) at its other input.

* * * * *